(12) United States Patent
Lemole, Jr. et al.

(10) Patent No.: US 11,090,002 B2
(45) Date of Patent: Aug. 17, 2021

(54) OCULAR CRANIAL NERVE MONITORING SYSTEM

(71) Applicant: ARIZONA BOARD OF REGENTS ON BEHALF OF THE UNIVERSITY OF ARIZONA, Tucson, AZ (US)

(72) Inventors: Gerald Michael Lemole, Jr., Tucson, AZ (US); Marek Romanowski, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 320 days.

(21) Appl. No.: 16/066,265

(22) PCT Filed: Jan. 23, 2017

(86) PCT No.: PCT/US2017/014552
§ 371 (c)(1),
(2) Date: Jun. 26, 2018

(87) PCT Pub. No.: WO2017/127798
PCT Pub. Date: Jul. 27, 2017

(65) Prior Publication Data
US 2020/0268321 A1 Aug. 27, 2020

Related U.S. Application Data

(60) Provisional application No. 62/286,052, filed on Jan. 22, 2016.

(51) Int. Cl.
*A61B 3/14* (2006.01)
*A61B 5/00* (2006.01)
(Continued)

(52) U.S. Cl.
CPC ............ *A61B 5/6821* (2013.01); *A61B 3/112* (2013.01); *A61B 3/14* (2013.01); *A61B 5/031* (2013.01);
(Continued)

(58) Field of Classification Search
CPC .. A61B 3/00; A61B 3/06; A61B 3/063; A61B 3/09; A61B 3/10; A61B 3/11;
(Continued)

(56) References Cited

U.S. PATENT DOCUMENTS 4,007,980 A * 2/1977 Bracher ................. A61B 3/112
351/219
5,297,554 A * 3/1994 Glynn .................... A61B 3/125
351/206

(Continued)

FOREIGN PATENT DOCUMENTS

| WO | WO1990012534 A1 | 11/1990 |
| WO | WO2013148557 A1 | 10/2013 |

OTHER PUBLICATIONS

Sanders RD. Cranial Nerves III, IV, and VI: Oculomotor Function. Psychiatry (Edgmont). Nov. 2009;6(11):34-9. PMID: 20049149; PMCID: PMC2801485.*

(Continued)

*Primary Examiner* — Eugene T Wu
(74) *Attorney, Agent, or Firm* — Nguyen Tarbet LLC

(57) ABSTRACT

An ocular cranial nerve monitoring system (OCNMS) that provides continuous measurement of pupillary reactivity in the eye. The system features a sensor component that produces a stimulating light and a recording light and records reflected recording light so as to calculate pupillary diameter and response to stimulation as measured by latency, velocity, and/or amplitude. This system of the present invention may be used for indirect assessment of the (Continued)

2nd and 3rd cranial nerve (CN 2, CN3) pathways and/or intracranial pressure in patients and may be used intraoperatively. The data obtained from this system may allow for immediate corrective actions, which may help prevent permanent deficits and improve patient safety and surgical outcomes. In some instances, the system may help avoid unnecessary or invasive procedures (e.g., catheters inserted for intracranial pressure monitoring).

16 Claims, 4 Drawing Sheets

(51) Int. Cl.
    *A61B 3/11*     (2006.01)
    *A61B 5/03*     (2006.01)
    *A61B 5/389*     (2021.01)

(52) U.S. Cl.
    CPC ............ *A61B 5/389* (2021.01); *A61B 5/4047* (2013.01); *A61B 2562/0233* (2013.01); *A61B 2562/164* (2013.01)

(58) Field of Classification Search
    CPC .......... A61B 3/112; A61B 3/125; A61B 3/14; A61B 5/0059; A61B 5/0082; A61B 5/031; A61B 5/1103; A61B 5/1106; A61B 5/4029; A61B 5/4035; A61B 5/4041; A61B 5/4047; A61B 5/4052; A61B 5/4821; A61B 5/6821
    See application file for complete search history.

(56) References Cited

U.S. PATENT DOCUMENTS

| | | | |
|---|---|---|---|
| 6,306,100 | B1 | 10/2001 | Prass |
| 6,631,989 | B2 | 10/2003 | Odom et al. |
| 6,820,979 | B1* | 11/2004 | Stark ...................... A61B 3/112 351/206 |
| 7,731,360 | B2 | 6/2010 | MacDougall et al. |
| 7,801,271 | B2 | 9/2010 | Gertner et al. |
| 7,802,900 | B2 | 9/2010 | Suba |
| 7,854,511 | B2 | 12/2010 | Molnar et al. |
| 7,988,287 | B1 | 8/2011 | Butler et al. |
| 8,255,045 | B2 | 8/2012 | Gharib et al. |
| 8,668,337 | B2 | 3/2014 | Waldorf et al. |
| 2008/0212026 | A1 | 9/2008 | Molnar et al. |
| 2010/0240971 | A1 | 9/2010 | Zanatta et al. |
| 2011/0077548 | A1 | 3/2011 | Torch |
| 2013/0235346 | A1 | 9/2013 | Huang et al. |
| 2013/0250244 | A1 | 9/2013 | Yao et al. |
| 2014/0185010 | A1* | 7/2014 | Bernert .................. A61B 3/112 351/219 |
| 2014/0276195 | A1 | 9/2014 | Papay et al. |
| 2018/0235456 | A1* | 8/2018 | Karakaya ............. A61B 5/4824 |

OTHER PUBLICATIONS

Chambers, Rheagan Alexia. "Pupillary Device Design For Ocular Cranial Nerve Monitoring". Master's thesis. University of Arizona. 2018. https://repository.arizona.edu/handle/10150/628094.*
Rheagan Chambers, Nick Quon, Bridget Slomka, Nikolay Martirosyan, Michael Lemole Jr., Marek Romanowski, "Pupillary sensor for ocular cranial nerve monitoring," Proc. SPIE 11225, Clinical and Translational Neurophotonics 2020, 112250I (Feb. 17, 2020); https://doi.org/10.1117/12.2542058.*
Chateau et al. Infrared pupillometry in presbyopes filled with soft contact lenses. Optom Vis Sci. Dec. 1996;73 (12):733-41.
Smith. Google's new wearable project is a smart contact lens with medical uses. http://www.engadget.com/2014/01/16/google-smart-contact-lens/ Jan. 16, 2014.
Martinez-Ricarte, F. Infrared pupillometry. Basic principles and their application in the non-invasive monitoring of neurocritical patients. vol. 28. No. 1. Jan.-Feb. 2013.
Lu et al. Computerized mouse pupil size measurement for pupillary light reflex analysis. Computer Methods and Programs in Biomedicine, vol. 90, Issue 3, Jun. 2008, pp. 202-209.
Kumar et al. Quantitative analysis of pupillary light reflex by real-time autofluorescent imaging in a diabetic mouse model. Experimental Eye Research vol. 92, Issue 3, Mar. 2011, pp. 164-172.
Daluwatte et al. Simultaneously measured pupillary light reflex and heart rate variability in healthy children. Physiol Meas. Jun. 2012; 33(6): 1043-1052.
Liem. MedScape: Intraoperative Neurophysiological Monitoring. Oct. 18, 2012. http://emedicine.medscape.com/article/1137763-overview#showall.
Dinalankara et al. rPLR: an imaging system for measuring pupillary light reflex at a distance. Applied Optics, Nov. 10, 2014 / vol. 53, No. 32.
Chen et al. Infrared pupillometry, the Neurological Pupil index and unilateral pupillary dilation after traumatic brain injury: implications for treatment paradigms. SpringerPlus 2014, 3:548.
Taylor et al. Quantitative pupillometry, a new technology: normative data and preliminary observations in patients with acute head injury. J Neurosurg 98:205-213, 2003.
Chen et al. Pupillary reactivity as an early indicator of increased intracranial pressure: The introduction of the Neurological Pupil index. Surgical Neurology International 2011, 2:82.
Fison et al. Assessment of unilateral afferent pupillary defects by pupillography.British Journal of Ophthalmology, 1979, 63, 195-199.
Yan et al. Clinical Utility of an Automated Pupillometer for Assessing and Monitoring Recipients of Liver Transplantation. Liver Transplantation 15:1718-1727, 2009.
Wilhelm et al. Clinical Applications of Pupillography. J Neuro-Ophthalmol, vol. 23, No. 1, 2003.
Ortube et al. Comparative Regional Pupillography as a Noninvasive Biosensor Screening Method for Diabetic Retinopathy. Investigative Ophthalmology & Visual Science, Jan. 2013, vol. 54, No. 1.
Koehler et al. Fixed and dilated: the history of a classic pupil abnormality. J Neurosurg 122:453-463, 2015.
Sautter et al. GM1 ganglioside treatment reduces visual deficits after graded crush of the rat optic nerve. Brain Research, 565 (1991) 23-33.
Lee et al. Development of Pupillography Using Image Processing. Korean J Ophthalmol vol. 19, No. 2, 2005.
Bergamin et al. Latency of the Pupil Light Reflex: Sample Rate, Stimulus Intensity, and Variation in Normal Subjects. Investigative Ophthalmology & Visual Science, Apr. 2003, vol. 44, No. 4.
Klocker et al. Morphological and functional analysis of an incomplete CNS fiber tract lesion: Graded crush of the rat optic nerve. Journal of Neuroscience Methods 110 (2001) 147-153.
Swanson et al. Neuroprotective Effect of Sulfhydryl Reduction in a Rat Optic Nerve Crush Model. Investigative Ophthalmology & Visual Science, Oct. 2005, vol. 46, No. 10.
You et al. Anterograde Degeneration along the Visual Pathway after Optic Nerve Injury. PLOS ONE, Dec. 2012 vol. 7 | Issue 12 | e52061.
Thompson. Otto Lowenstein, Pioneer Pupillographer. J Neuro-Ophthalmol, vol. 25, No. 1, 2005.
Zhu et al. The Role of Peroxisome Proliferator-Activated Receptor and Effects of Its Agonist, Pioglitazone, on a Rat Model of Optic Nerve Crush: PPARc in Retinal Neuroprotection. PLOS ONE, Jul. 2013 | vol. 8 | Issue 7 | e68935.
Bremner. Pupil assessment in optic nerve disorders. Eye (2004) 18, 1175-1181.
Ellis. The pupillary light reflex in normal subjects. British Journal of Ophthalmology, 1981, 65, 754-759.
Papageorgiou et al. Pupil Perimetry Demonstrates Hemifield Pupillary Hypokinesia in a Patient With a Pretectal Lesion Causing a Relative Afferent Pupil Defect but No Visual Field Loss. J Neuro-Ophthalmol, vol. 29, No. 1, 2009.
Fountas et al. Clinical Implications of Quantitative Infrared Pupillometry in Neurosurgical Patients. Neurocritical Care, vol. 5, 2006.

(56) References Cited

OTHER PUBLICATIONS

Gellrich et al. Quantification of histological changes after calibrated crush of the intraorbital optic nerve in rats. Br J Ophthalmol 2002 86: 233-237.
Frazen et al. Sleep deprivation alters pupillary reactivity to emotional stimuli in healthy young adults. Biol Psychol. Mar. 2009 ; 80(3): 300-305.
Warga et al. How do spontaneous pupillary oscillations in light relate to light intensity? Vision Research 49 (2009) 295-300.
Kim et al. Neuroprotective effect of transpupillary thermotherapy in the optic nerve crush model of the rat. Eye (2009) 23, 727-733.
Ma et al. Neuroprotective effect on retinal ganglion cells by transpupillary laser irradiation of the optic nerve head. Neuroscience Letters 476 (2010) 3-8.

* cited by examiner

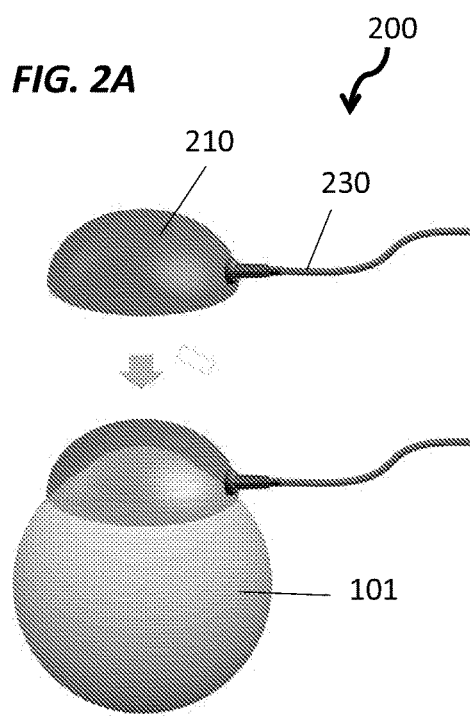
FIG. 2A
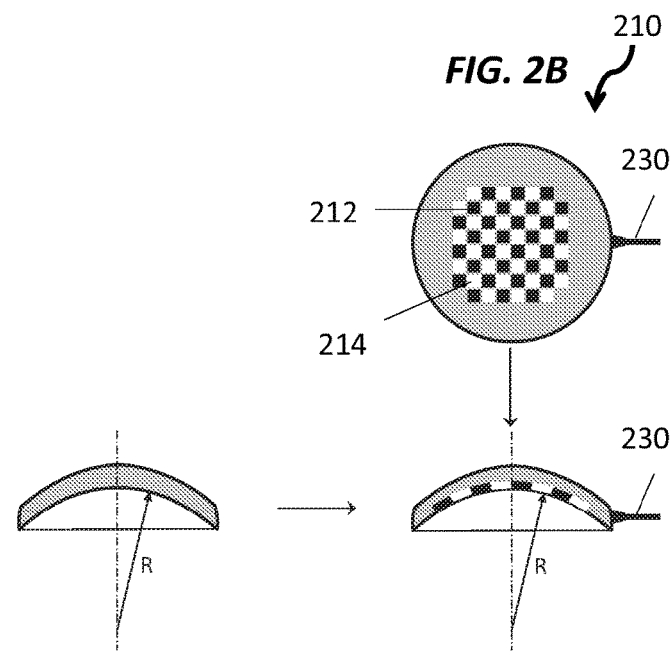
FIG. 2B
FIG. 2C
FIG. 2D
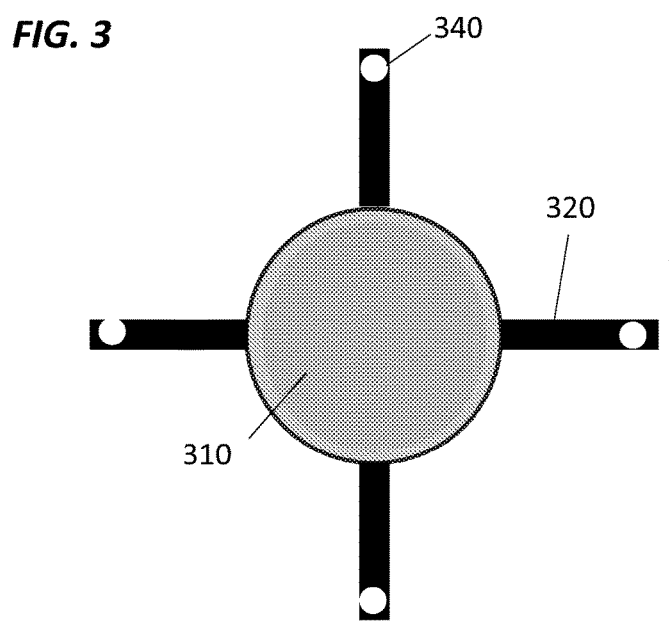
FIG. 3

FIG. 4A
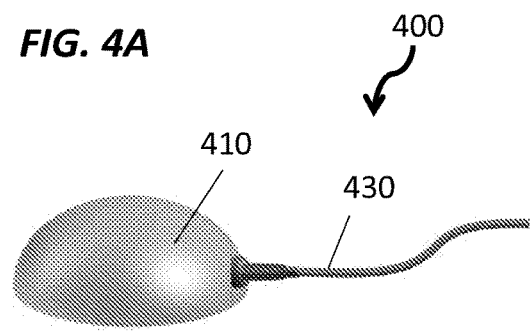
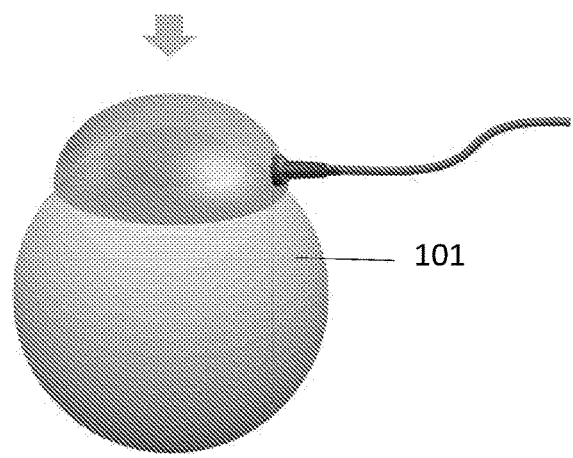
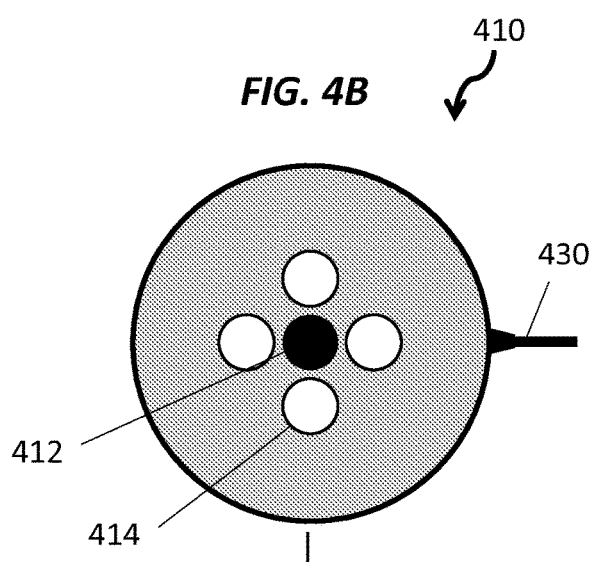
FIG. 4B
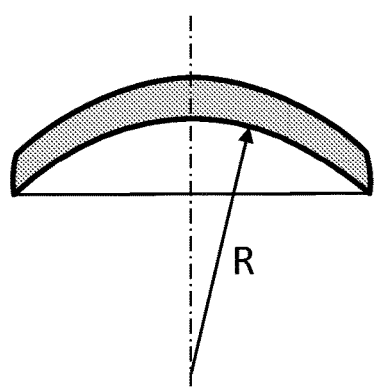
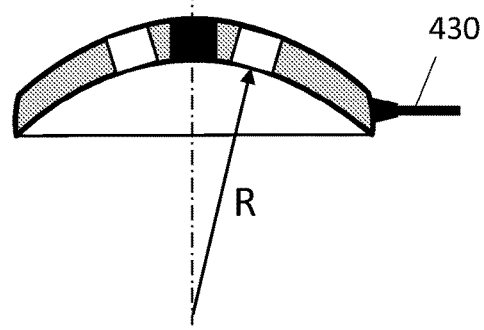
FIG. 4C
FIG. 4D

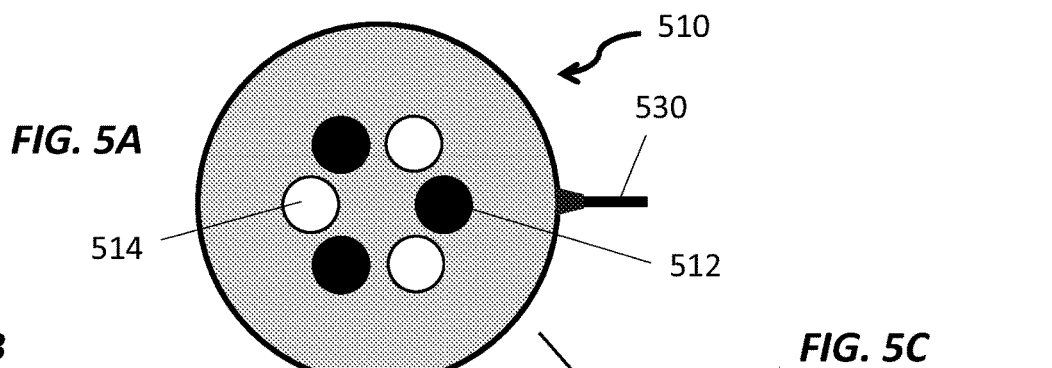
FIG. 5A
FIG. 5B
FIG. 5C
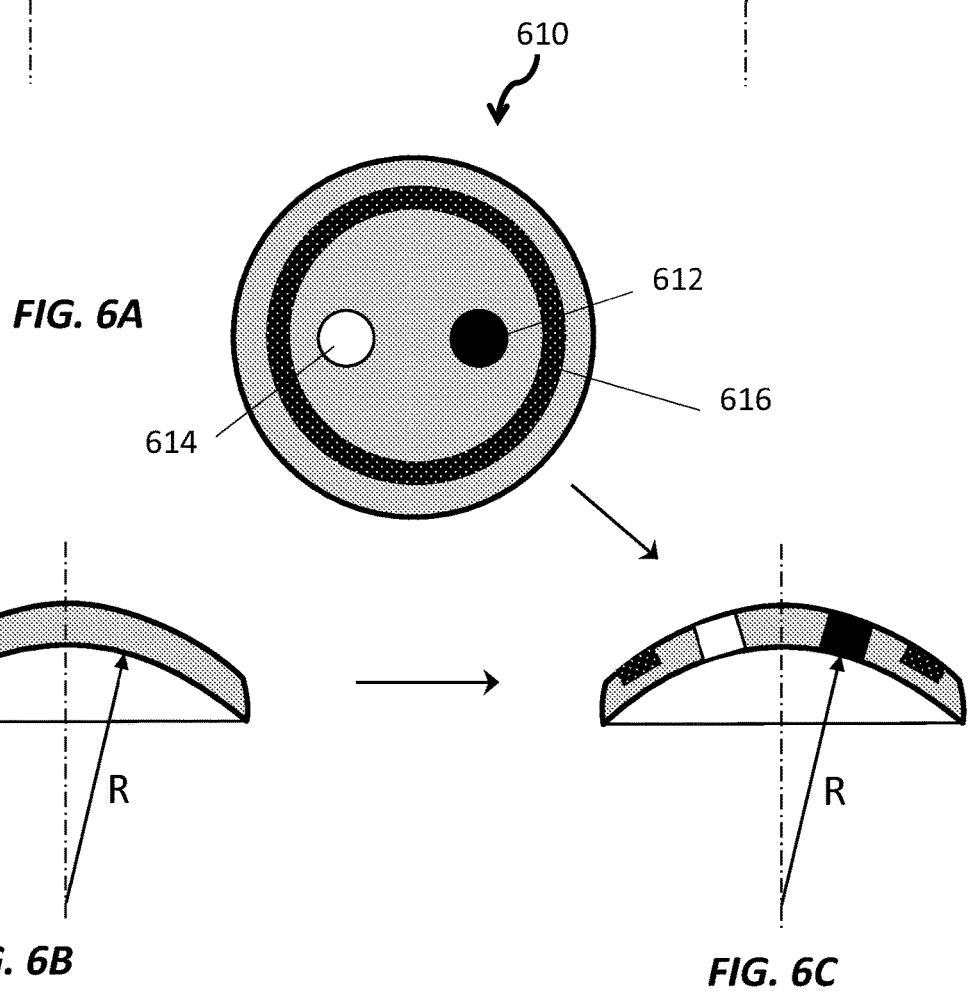
FIG. 6A
FIG. 6B
FIG. 6C

US 11,090,002 B2

OCULAR CRANIAL NERVE MONITORING SYSTEM

CROSS REFERENCE

This application claims priority to U.S. Patent Application No. 62/286,052, filed Jan. 22, 2016, the specification(s) of which is/are incorporated herein in their entirety by reference.

FIELD OF THE INVENTION

The present invention relates to methods and systems for measuring pupillary light reflex responses (pupillometry), more particularly to a device or system featuring a solid-state camera and light source (e.g., visible, infrared) mounted onto an extraocular lens/shield for measuring pupillary light reflex responses, e.g., bilaterally, in real-time or near real-time. The system may be used, e.g., intraoperatively, to determine the integrity of one or more cranial nerves, e.g., $2^{nd}$ and/or $3^{rd}$ cranial nerve, as well as to infer intracranial pressure and measure ocular muscle activity.

BACKGROUND OF THE INVENTION

Electrophysiological monitoring of motor, sensory, and cranial nerve function is routine for many neurosurgical procedures. These techniques quantify changes in stimulatory current and resulting amplitude of EEG or muscular activity. With cranial nerves in particular, somatic motor nerves (cranial nerves (CNs) 12, 11, 10/9, 7, 5) and some special sensory nerves (CN 8) are readily monitored for feedback during complex surgical procedures in those respective regions. The upper cranial nerves, however, remain more difficult to monitor. Cranial nerves 3 and 4 do have motor tracts but placement of a needle lead into their respective extraocular muscles can be difficult. Assessment of the optic nerves (CN 2) remains even more problematic because the most often used modality, visual evoked potentials (VEP), measures not only nerve integrity, but also that of the optic tracts and visual cortex. In practice it has not been found to be entirely reliable. The eyes are a vital window to the function and health of the central nervous system and brain. Pupillary reflexes, extraocular motor function, and direct retinal inspection can all provide invaluable information ranging from cranial nerve, tract, and nuclei integrity to an indirect measure of intracranial pressure. Indeed, cranial nerve function has been used to assess intracranial pressure in critical ICU patients and attempts have been made to correlate brainstem auditory evoked responses (BAERs, e.g., CN 8) and intermittent/periodic reflex pupillometry (CN 3) with intracranial pressure. The current state-of-the-art in reflex pupillometry involves hand-held devices based on 40 year-old technology. A brief light source illuminates the retina, and subsequent pupillary response (including latency, velocity, and amplitude) is recorded with an infrared light-source and camera. These measurements are intermittent and require logistically difficult manipulations including manual eyelid opening and measurement of the contralateral response. In the clinic setting with awake patients, these impediments are easily overcome; however, in the ICU or OR with critical and comatose patients or anesthetized patients, such interventions are not often feasible.

The present invention features an ocular cranial nerve monitoring system (OCNMS), e.g., an on-eye or near-eye (e.g. contact lens or shield) reflex pupillometry device that can provide continuousmeasurement (e.g., real-time or near real-time measurement) of the eye (a pair of systems is used for monitoring both eyes. Briefly, the system features the use of a stimulating light (e.g., white light) and a recording light (e.g., infrared light) as well as a camera design for continuously measuring pupillary diameter and response to stimulation as measured by latency, velocity, and/or amplitude, and/or any other appropriate parameters. This monitoring modality can record both ipsilateral and contralateral (consensual) pupillary responses simultaneously when the device is employed over both eyes; this is an important distinction compared to existing technology. This may allow for an indirect assessment of the $2^{nd}$ and $3^{rd}$ cranial nerve (CN 2, CN3) pathways and indirectly measure intracranial pressure. The system of the present invention (OCNMS) may be used intraoperatively, e.g., in anesthetized patients, or in comatose and/or neurologically compromised patients (e.g., patients in the ICU). (The system may also be able to be used on awake patients.) As such, the system can be used to provide immediate feedback concerning manipulations of particular nerves, e.g., CN 2, CN3) and/or the brainstem. The system or the present invention (OCNMS) may also be used to provide feedback concerning intracranial pressure. This feedback may allow for immediate corrective actions, which may help prevent permanent deficits and improve patient safety and surgical outcomes. In some instances, this feedback may help avoid unnecessary or invasive procedures (e.g., Ventriculostomy catheters inserted for intracranial pressure monitoring).

The present invention also features applications and methods of use of said ocular cranial nerve monitoring system. For example, in some embodiments, the OCNMS is used during anterior skull base procedures (e.g., transnasal, transcranial) so as to provide immediate feedback as particular cranial nerves (e.g., CN 2, CN3) were manipulated, potentially limiting damage by alerting the surgeon to the impending insult. In some embodiments, the OCNMS may also allow for a more reliable stimulation and measurement of visual evoked potentials (VEP) to assess the integrity of the entire visual pathway (retina to cortex).

In some embodiments, the system of the present invention is used for monitoring intracranial pressure in patients with severe traumatic brain injury (TBI) or malignant cerebral edema (or other appropriate conditions), e.g., in the ICU. For example, patients with severe TBI or malignant cerebral edema are at risk for severe disability or death from progressive intracranial hypertension. Historical observations ("blown pupil") and recent pupillometry literature suggest that subtle pupillary dysfunction (increased latency, decreased velocity) presages rising intracranial pressure. Continuously recording these parameters using the system of the present invention may allow earlier interventions (e.g., diuretics, barbiturate coma, decompressive craniectomy) before irreversible damage has occurred.

The system of the present invention may also be used as a predictor of elevated intracranial pressure, e.g., to predict the patients that would require invasive monitoring and/or intervention in the first place. This may help provide appropriate intervention in a timely and effective manner so as to help avoid poor or worsening outcomes. This may also help avoid the use of said invasive procedures (e.g. Ventriculostomy) in individuals that did not need them, thereby limiting primarily hemorrhagic and infectious risks. The system may also help function to prognosticate a patient's outcome, e.g., a traumatic brain injury patient's outcome.

SUMMARY OF THE INVENTION

The present invention features ocular cranial nerve monitoring systems for monitoring pupillary reactivity. In some embodiments, the system comprises a sensor component comprising a plurality of image sensors and a plurality of light emitters disposed on a sensor component surface. The light emitters may be adapted to emit a stimulating light and a recording light, wherein the stimulating light has a wavelength that is effective for triggering pupil reactivity. The image sensors may be adapted to detect recording light reflected from the iris. The system may (or may not) further comprise an intermediate plate having a sensor surface connected to the sensor surface of the sensor component and an eye surface for placing atop the eye, the eye surface being curved, wherein the intermediate plate allows or promotes transmission of recording light reflected from the iris to the image sensors. The system may further comprise a computer system operatively connected to the image sensors, wherein the computer system is adapted to calculate a pupillary reactivity parameter based on recording light detected by the image sensors. In some embodiments, the sensor component is curved to accommodate the curvature of the eye. In some embodiments, the system continuously activates the sensor component so as to obtain continuous measurements of the pupillary reactivity parameter.

In some embodiments, the system is used to monitor intracranial pressure. In some embodiments, the system is used to monitor intracranial pressure intraoperatively. In some embodiments, the system is used to monitor cranial nerve (CN) 2, CN 3, or both CN 2 and CN 3 integrity or function. In some embodiments, the image sensor (112) comprises a complementary metal-oxide-semiconductor (CMOS) sensor, a wafer-layer optic (WLO) sensor, or a wafer-level packaging (WLP) sensor. In some embodiments, the light emitter, the image sensors, or both the light emitter and the image sensors comprise OLED-on-silicon technology. In some embodiments, the recording light is infrared light or ambient light or visible light. In some embodiments, the wavelength of the recording light is from 400 to 700 nm. In some embodiments, the pupillary reactivity parameter is velocity and/or amplitude and/or latency.

In some embodiments, the image sensors and light emitters are arranged on the sensor surface in an alternating pattern. In some embodiments, the alternating pattern is a checkerboard pattern, a radial pattern, or a diagonal pattern. In some embodiments, the image sensors and light emitters are arranged on the sensor surface such that they do not obstruct a line of sight extending through an apex of the sensor component. In some embodiments, the image sensors and light emitters are arranged on the sensor surface at locations that do not obstruct central vision, paracentral vision, or near peripheral vision.

In some embodiments, the intermediate plate comprises a bundle of optical fibers. In some embodiments, the intermediate plate comprises a zero-depth optical window. In some embodiments, the zero-depth optical window comprises a bundle of optical fibers. In some embodiments, the optical fibers comprise a multi-fiber plate, a fiber optic plate, a fiber optic faceplate, or a fiber optic taper. In some embodiments, the intermediate plate is hollow. In some embodiments, the intermediate plate matches curvature of an eye to allow surface tension to hold the system in place when placed on the eye. In some embodiments, the intermediate plate is disposable.

In some embodiments, the system further comprises extensions extending from one or more sides of the sensor component, wherein electrodes are disposed on ends of the extensions, the electrodes function to stimulate muscles around the eye. In some embodiments, the electrodes are operatively connected to the computer processing system. In some embodiments, the computer system is operatively connected to the sensors via a wireless mechanism. In some embodiments, the wireless mechanism comprises a radio-frequency identification (RFID) system. In some embodiments, the wireless mechanism is for collecting measurements of the pupillary reactivity. In some embodiments, the wireless mechanism is for providing power to the image sensor or the light emitters. In some embodiments, the sensor surface comprises a rigid support material. In some embodiments, the rigid support material comprises polymethyl methacrylate (PMMA), polystyrene (PS), or a combination thereof. In some embodiments, the sensor surface comprises a flexible support material. In some embodiments, the flexible support material comprises a polymer adapted for flexible electrodes. In some embodiments, the flexible support material comprises polyimide (PI), polyethylene terephthalate (PET), polyether ether ketone (PEEK), or a combination thereof. In some embodiments, the sensor surface comprises a combination of a rigid support material and a flexible support material. In some embodiments, the sensor surface matches curvature of an eye to allow surface tension to hold the system in place when placed on the eye.

The present invention also features methods of detecting pupillary reactivity. In some embodiments, the method comprises activating on a patient an ocular cranial nerve monitoring system of the present invention. In some embodiments, the light emitters emit stimulating light and recording light to the iris and pupil, wherein the stimulating light triggers pupil reaction, the sensors detect recording light reflected from the iris, and the computer system calculates a pupillary reactivity parameter based on recording light detected by the sensors.

The present invention also features methods of monitoring of intracranial pressure. In some embodiments, the method comprises activating on a patient an ocular cranial nerve monitoring system according to the present invention. In some embodiments, the light emitters emit stimulating light and recording light to the iris and pupil, the stimulating light triggers pupil reaction, the sensors detect recording light reflected from the iris, and the computer system calculates a pupillary reactivity parameter based on recording light detected by the sensors, wherein the pupillary reactivity parameter is indicative of intracranial pressure.

The present invention also features methods of monitoring of integrity or function of cranial nerve (CN) 2, CN 3, or CN 2 and CN3. In some embodiments, the method comprises activating on a patient an ocular cranial nerve monitoring system according to the present invention. In some embodiments, the light emitters emit stimulating light and recording light to the iris and pupil, the stimulating light triggers pupil reaction, the sensors detect recording light reflected from the iris, and the computer system calculates a pupillary reactivity parameter based on recording light detected by the sensors, wherein the pupillary reactivity parameter is indicative of CN 2, CN 3, or CN 2 and CN3 integrity or function.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 1C shows the processing of an intermediate plate (e.g., an optical fiber plate): an unprocessed optical fiber plate (flat).

FIG. 1D shows the processing of an intermediate plate (e.g., an optical fiber plate): an optical fiber plate processed to conform to the eyeball curvature or similar.

FIG. 1E shows the processing of an intermediate plate (e.g., an optical fiber plate): a processed optical fiber plate with the sensor (e.g., OLED-on-silicon sensor) attached.

FIG. 2A shows a perspective view of an embodiment of the ocular cranial nerve monitoring system (OCNMS) of the present invention. For example, the system may comprise a meniscus lens incorporating OLED-on-silicon pixels that can send light and capture images. The system may have a generally concave curvature that conforms to the shape of the eye or similar.

FIG. 2B shows a schematic view of the sensor, e.g., an OLED-on-silicon sensor (a bottom view, e.g., as viewed from the optical plate). The black squares represent CMOS sensors, and the white squares represent OLED emitter (e.g., visible or NIR, etc.). The pattern of sensors and emitters may be checkerboard or any other appropriate pattern not limited to those patterns disclosed herein.

FIG. 2C shows the processing of a lens (e.g., PMMA, etc.): an unprocessed lens.

FIG. 2D shows the processing of a lens (e.g., PMMA, etc.): a lens processed with the sensor (e.g., OLED-on-silicon sensor) attached.

FIG. 3 shows an alternative embodiment (a top view) of the system of the present invention. The system comprises extensions that may feature electrodes for contacting muscle fibers around the eye to facilitate EMG monitoring modalities.

FIG. 4A shows a perspective view of an embodiment of the ocular cranial nerve monitoring system (OCNMS) of the present invention.

FIG. 4B shows a wired image sensor (as viewed from the bottom). The black circle is a wafer-level optics (WLO) technology image sensor, and the white circle is an LED emitter (e.g., visible, NIR, etc.). The pattern of white and dark circles is shown as an example. The present invention is not limited to this configuration.

FIG. 4C shows an unprocessed lens (e.g., PMMA, etc.).

FIG. 4D shows a processed lens with embedded wafer-level optics (WLO) sensors (black) and LED emitters (white).

FIG. 5A shows a wired image sensor (as viewed from the bottom). The black circle is a wafer-level optics (WLO) technology image sensor, and the white circle is an LED emitter (e.g., visible, NIR, etc.). The pattern shown is not obstructing central vision. The pattern of white and dark circles is shown as an example. The present invention is not limited to this configuration.

FIG. 5B shows an unprocessed lens (e.g., PIMA, etc.).

FIG. 5C shows a processed lens with embedded wafer-level optics (WLO) sensors (black) and LED emitters (white).

FIG. 6A shows a wired image sensor (as viewed from the bottom). The black circle is a wafer-level optics (WLO) technology image sensor, and the white circle is an LED emitter (e.g., visible, NIR, etc.). The dotted ring is an RFID antenna. The pattern shown is not obstructing central vision. The pattern of white and dark circles is shown as an example. The present invention is not limited to this configuration.

FIG. 6B shows an unprocessed lens (e.g., PMMA, etc.).

FIG. 6C shows a processed lens with embedded wafer-level optics (WLO) sensors (black), LED emitters (white), and an antenna added (dotted).

DETAILED DESCRIPTION OF THE INVENTION

The present invention features an ocular cranial nerve monitoring system (OCNMS), e.g., an on-eye or near-eye reflex pupillometry device that can provide continuous measurement (e.g., real-time or near real-time measurement) of the eye (a pair of systems is used for monitoring both eyes). As previously discussed, the system features the use of a stimulating light (e.g., a pulse of light) and a recording light (e.g., infrared light) as well as a sensor/camera design for continuously measuring pupillary diameter and response to stimulation (e.g., as measured by latency, velocity, and/or amplitude, and/or any other appropriate parameters). This may allow for an indirect assessment of the $2^{nd}$ and $3^{rd}$ cranial nerve (CN 2, CN3) pathways and monitoring of intracranial pressure.

Embodiment 1

Figure 1A:
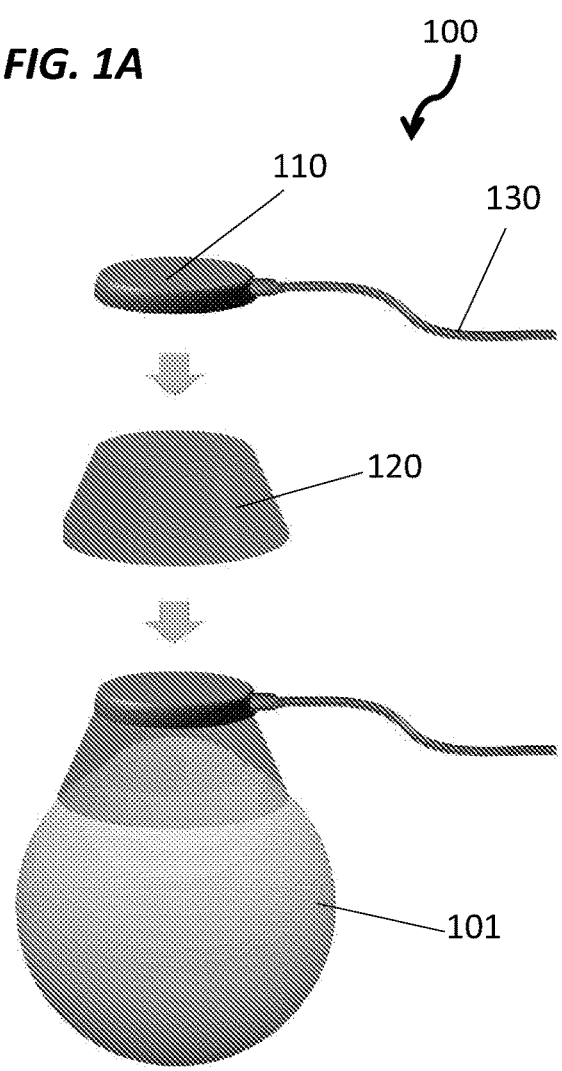
FIG. 1A shows a perspective view of an embodiment of the ocular cranial nerve monitoring system (OCNMS) of the present invention. For example, the system may comprise sensor (e.g., an OLED-on-silicon sensor) that sends light and captures images. The system may further comprise an intermediate plate (e.g., an optical fiber plate, optionally disposable) that may match the eyeball's curvature (or similar) and size to the sensor. In some embodiments, the system is assembled using adhesives, such as PVA adhesives. The system may be placed on the eyeball as shown in FIG. 1A.
Figure 1B:
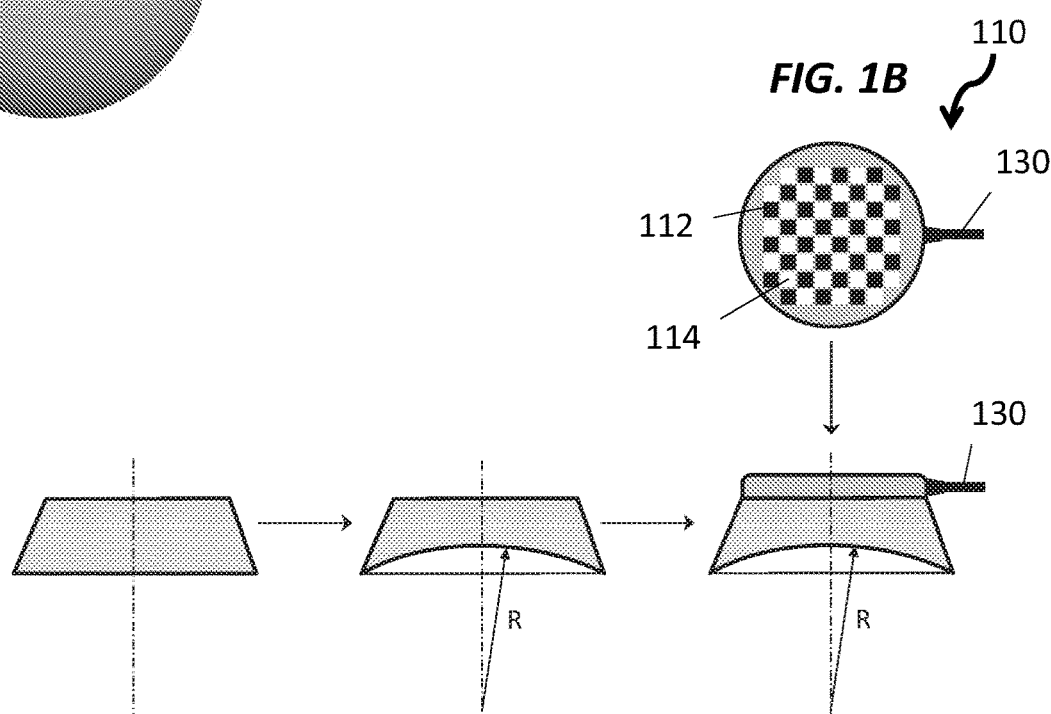
FIG. 1B shows a schematic view of the sensor, e.g., an OLED-on-silicon sensor (a bottom view, e.g., as viewed from the intermediate plate or optical fiber plate). The black squares represent CMOS sensors, the white squares represent OLED emitter (e.g., visible or NIR, etc.). The pattern of sensors and emitters may be checkerboard or any other appropriate pattern not limited to those patterns disclosed herein.

Referring to FIG. 1A, FIG. 1B, FIG. 1C, FIG. 1D, and FIG. 1E, in some embodiments, the ocular cranial nerve monitoring system (OCNMS) (100) comprises a sensor component (110). The sensor component (110) is adapted to send a pulse of light, e.g., the stimulating light (e.g., white/visible light) and sense or capture images via a recording light (e.g., infrared light). For example, in some embodiments, the sensor component (110) comprises image sensors (112) and light emitters (114). The image sensors (112) may comprise complementary metal-oxide-semiconductor (CMOS) sensors; however, the image sensors (112) are not limited to CMOS sensors. In some embodiments, the light emitters (114) comprise organic light emitting diodes (OLEDs); however, the light emitters (114) are not limited to OLEDs. In some embodiments, the sensor component (110) comprises an OLED-on-silicon sensor. In some embodiments, the light emitters (114) can emit light of one or more wavelengths, e.g., visible, infrared (IR), near infrared (NIR), etc. The light emitters (114) and image sensors (112) may be arranged in any appropriate configuration such as but not limited to a checkerboard configuration shown in FIG. 1B. The present invention is not limited to this configuration.

As previously discussed, the light emitters (114) provide a stimulating light and a recording light. In some embodiments, the stimulating light comprises white light or any particular visible light. For example, in some embodiments, the stimulating light has a wavelength between 400 nm and 700 nm. In some embodiments, the stimulating light has a wavelength between 400 and 800 nm. In some embodiments, the stimulating light has a wavelength between 380 and 700 nm. In some embodiments, the stimulating light has a wavelength between 380 and 800 nm. In some embodiments, the recording light comprises infrared light. For example, in some embodiments, the recording light has a wavelength between 700 nm and 15 µm. In some embodiments, the recording light has a wavelength between 800 nm and 15 µm. In some embodiments, the recording light has a wavelength between 700 nm and 1400 nm. In some embodiments, the recording light has a wavelength between 750 nm and 1400 nm. In some embodiments, the recording light has a wavelength between 1400 nm and 3 µm. In some embodiments, the recording light has a wavelength between 3 µm and 8 µm. In some embodiments, the recording light has a wavelength between 8 µm and 15 µm. In some embodiments, the recording light has a wavelength between 15 µm and 30 µm. In some embodiments, the recording light is visible light.

The sensor component (110) may provide the stimulating light, which triggers pupil reaction. The sensor component (110) may simultaneously function as a camera or sensor for detecting the recording light (e.g., IR light). The sensor component (110) may be adapted to measure pupil area or diameter, and may detect the velocity and latency (e.g., lag or wait time). For example, the IR light that bounces off the eye may detected, whereas the IR light that continues through the pupil may not be detected. Based on what is detected, the system may calculate the appropriate pupil reactivity parameters. The system may measure this pupillary response simultaneously in both pupils (e.g., ipsilateral and consensual) if the monitoring devices are employed over both eyes. As previously discussed, this is an important distinction compared with existing technologies.

The system (100) of the present invention may feature components or systems that can filter out or differentiate between recording light that is reflected off the retina from that which is reflected from the iris. The system (100) may further comprise an intermediate plate (120) for adapting the sensor component (110) to the eye (101). The intermediate plate (120) provides a means of adapting the sensor component (110) to the curvatures and/or sizes of the eye. The intermediate plate (120) can also help to block any interfering light from accidentally interfering with the sensor component (110), e.g., the intermediate plate (120) provides a dark environment for the light pulses and recordings.

The intermediate plate (120) has a sensor surface that attaches or connects to the sensor component (110). The intermediate plate also has an eye surface (a curved surface) that is for placing atop the eye. In some embodiments, the intermediate plate comprises optical fibers (e.g., a bundle of optical fibers) that transmit light, e.g., the intermediate plate is an optical fiber plate. In some embodiments, the intermediate plate is hollow. The intermediate plate (120) is not limited to the aforementioned configurations and may comprise any appropriate components that allow for the image capturing of the eye via the sensor component (110). In some embodiments, the optical fibers may be narrowed (or tapered) so as to change the size of the field or image. In some embodiments, the intermediate plate (120) is disposable. In some embodiments, the sensor surface of the intermediate plate (120) is attached to the sensor component (110) via any appropriate adhesive or lubricant. In some embodiments, the intermediate plate (120) matches the curvature of the eye to allow surface tension to hold the system in place when placed on the eye, e.g., like a contact lens.

In some embodiments, the system (100), e.g., the sensor component (110), is operatively connected to a computer processing system and/or a power source via a wire (130) (e.g., for cost-effectiveness). In some embodiments, the system (100), e.g., the sensor component (110), is wirelessly operatively connected to a computer processing system. In some embodiments, the sensor component (110) comprises a battery system. In some embodiments, the sensor component (110) functions as a camera. In some embodiments, the sensor component (110) is operatively connected to a camera. In some embodiments, the sensor component (110) and/or camera is operatively connected to a computer system that is adapted to measure and records the pupillary constriction (latency, velocity, amplitude) and process the parameters appropriately to provide information usable to surgeons or other medical professionals.

Because the system of the present invention is adapted to measure pupillary reactivity on a continuous basis, the data obtained from the system of the present invention may be used to show trends wherein a normal reactivity changes to an abnormal reactivity. This may provide an indicator to the surgeon or medical professional that action should be taken, e.g., action related to the cranial nerve affected, action related to intracranial pressure, etc.

Embodiment 2

Referring to FIG. 2A, FIG. 2B, FIG. 2C, and FIG. 2D, in some embodiments, the ocular cranial nerve monitoring system (OCNMS) (200) comprises a sensor component (210) that is curved and adapted to contact the eye (101). For example, the system (200) may comprise a meniscus lens incorporating OLED-on-silicon pixels that can send light and capture images. The system (200) may have a generally concave curvature that conforms to the shape of the eye or similar. In some embodiments, the system (200), e.g., the sensor component (210) or other appropriate component, matches the curvature of the eye to allow surface tension to hold the system in place when placed on the eye (e.g., like a contact lens). In some embodiments, the system (200) comprises multiple chips and wires, creating an array configuration so as to accommodate the light emitters and sensors into a curved lens-like configuration.

As previously discussed, the sensor component (210) is adapted to send a pulse of light, e.g., the stimulating light (e.g., white/visible light) and sense or capture images via a recording light (e.g., infrared light). For example, in some embodiments, the sensor component (210) comprises image sensors (212) and light emitters (214). The image sensors (212) may comprise complementary metal-oxide-semiconductor (CMOS) sensors; however, the image sensors (212) are not limited to CMOS sensors. In some embodiments, the light emitters (214) comprise organic light emitting diodes (OLEDs); however, the light emitters (214) are not limited to OLEDs. In some embodiments, the sensor component (210) comprises an OLED-on-silicon sensor. In some embodiments, the light emitters (214) can emit light of one or more wavelengths, e.g., visible, infrared (IR), near infrared (NIR), etc. The light emitters (214) and image sensors (212) may be arranged in any appropriate configuration such as a checkerboard configuration shown in FIG. 1B. The present invention is not limited to this configuration.

As previously discussed, the light emitters provide a stimulating light and a recording light. In some embodiments, the stimulating light comprises white light or any particular visible light. For example, in some embodiments, the stimulating light has a wavelength between 400 nm and 700 nm. In some embodiments, the stimulating light has a wavelength between 400 and 800 nm. In some embodiments, the stimulating light has a wavelength between 380 and 700 nm. In some embodiments, the stimulating light has a wavelength between 380 and 800 nm. In some embodiments, the recording light comprises infrared light. In some embodiments, the recording light comprises visible light, e.g., 400 to 700 nm or similar. In some embodiments, the recording light comprises ambient light (e.g., a camera may be able to capture images with ambient light, e.g., without any added light). In some embodiments, the recording light has a wavelength between 700 nm and 1 mm. In some embodiments, the recording light has a wavelength between 800 nm and 1 mm. In some embodiments, the recording light has a wavelength between 700 nm and 1400 nm. In some embodiments, the recording light has a wavelength between 750 nm and 1400 nm. In some embodiments, the recording light has a wavelength between 1400 nm and 3 µm. In some embodiments, the recording light has a wavelength between 3 µm and 8 µm. In some embodiments, the recording light has a wavelength between 8 µm and 15 µm. In some embodiments, the recording light has a wavelength between 15 µm and 1 mm.

The sensor component (210) may provide the stimulating light, which triggers pupil reaction. The sensor component (210) may simultaneously function as a camera or sensor for detecting the recording light (e.g., IR light). The sensor component (210) may be adapted to measure pupil area or diameter, and may detect the velocity and latency (e.g., lag or wait time). For example, the IR light that bounces off the eye may be detected, whereas the IR light that continues through the pupil may not be detected. Based on what is detected, the system may calculate the appropriate pupil reactivity parameters. The system (200) of the present invention may feature components or systems that can filter out or differentiate between recording light that is reflected off the retina from that which is reflected from the iris.

As previously discussed, in some embodiments, the system (200), e.g., the sensor component (210), is operatively connected to a computer processing system and/or a power source via a wire (230) (e.g., for cost-effectiveness). In some embodiments, the system (200), e.g., the sensor component (210), is wirelessly operatively connected to a computer processing system. In some embodiments, the sensor component (210) comprises a battery system. As previously discussed, in some embodiments, the sensor component (210) functions as a camera. In some embodiments, the sensor component (210) is operatively connected to a camera. In some embodiments, the sensor component (210) and/or camera is operatively connected to a computer system that is adapted to measure and records the pupillary constriction (latency, velocity, amplitude) and process the parameters appropriately to provide information usable to surgeons or other medical professionals.

Because the system of the present invention is adapted to measure pupillary reactivity on a continuous basis, the data obtained from the system of the present invention may be used to show trends wherein a normal reactivity changes to an abnormal reactivity. This may provide an indicator to the surgeon or medical professional that action should be taken, e.g., action related to the cranial nerve affected, action related to intracranial pressure, etc.

Methods and Applications for Use

As previously discussed, the ocular cranial nerve monitoring system (OCNMS) of the present invention may be used intraoperatively, e.g., in anesthetized patients, or in comatose and/or neurologically compromised patients (e.g., patients in the ICU). (The system may also be able to be used on awake patients.) The system may be used to provide feedback regarding manipulations of particular nerves, e.g., CN 2, CN 3, etc., and/or intracranial pressure. As such, the present invention features methods of monitoring CN 2 and/or CN 3 and/or brainstem integrity and/or function. The present invention also features methods of monitoring intracranial pressure. The feedback obtained from the system of the present invention may allow for immediate corrective actions, which may help prevent permanent deficits and improve patient safety and surgical outcomes. In some instances, this feedback may help avoid unnecessary or invasive procedures (e.g., catheters inserted for intracranial pressure monitoring).

More specifically, in some embodiments, the system is used during anterior skull base procedures (e.g., transnasal, transcranial) so as to provide immediate feedback as particular cranial nerves (e.g., CN 2, CN3) were manipulated, potentially limiting damage by alerting the surgeon to the impending insult. In some embodiments, the OCNMS may also allow for a more reliable stimulation and measurement of visual evoked potentials (VEP) to assess the integrity of the entire visual pathway (retina to cortex).

In some embodiments, the system of the present invention is used for monitoring intracranial pressure in patients with severe traumatic brain injury (TBI) or malignant cerebral edema (or other appropriate conditions), e.g., in the ICU. For example, patients with severe TBI or malignant cerebral edema are at risk for severe disability or death from progressive intracranial hypertension. Historical observations ("blown pupil") and recent pupillometry literature suggest that subtle pupillary dysfunction (increased latency, decreased velocity) presages rising intracranial pressure. Continuously recording these parameters using the system of the present invention may allow earlier interventions (e.g., diuretics, barbiturate coma, decompressive craniectomy) before irreversible damage has occurred.

The system of the present invention may also be used as a predictor of elevated intracranial pressure, e.g., to predict the patients that would require invasive monitoring and/or intervention. This may help provide appropriate intervention in a timely and effective manner so as to help avoid poor or worsening outcomes. This may also help avoid the use of said invasive procedures in individuals that did not need them. The system of the present invention may also be used in other applications, for example in epilepsy or seizure monitoring applications. In some embodiments, the system of the present invention may be used for multiple sclerosis applications. In some embodiments, the system may be used to monitory any condition wherein a change in reactivity of the pupils is indicative of a particular outcome.

Additional Features

The system of the present invention is not limited to the configurations shown and described herein. In some embodiments, the system further comprises an irrigation port to help moisten or lubricate the cornea. In some embodiments, the system may also be fitted with additional neuro-physiologic monitoring modalities such as the capability to display light patterns for use with visual evoked potential (VEP) monitoring. In some embodiments, the system comprises additional electrodes around the periphery, which might also allow sensing and stimulation of electrical current in the extraocular muscles so that cranial nerves 3, 4, and 6 might also be assessed for motor integrity. For example, referring to FIG. 3, in some embodiments, the ocular cranial nerve monitoring system (OCNMS) (300) comprises extensions (320) extending from one or more sides of the sensor component (310). The extensions (320) may comprise electrodes (340) that can contact muscle fibers around the eye. The electrodes (340) may be operatively connected to the sensor component (310) and/or a computer processing system. The electrodes (340) may allow for monitoring CN 4 and/or CN6 integrity and/or function.

Additional Embodiments

Referring to FIG. 4A, FIG. 4B, FIG. 4C, and FIG. 4D, in some embodiments, the ocular cranial nerve monitoring system (OCNMS) (400) comprises a sensor component (410) that is curved and adapted to contact the eye (101). For example, the system (400) may comprise a meniscus lens incorporating components that can send light and capture images. The system (400) may have a generally concave curvature that conforms to the shape of the eye or similar. In some embodiments, the system (400), e.g., the sensor component (410) or other appropriate component, matches the curvature of the eye to allow surface tension to hold the system in place when placed on the eye (e.g., like a contact lens). In some embodiments, the system (400) comprises multiple chips and wires, creating an array configuration so as to accommodate the light emitters and sensors into a curved lens-like configuration.

As previously discussed, the sensor component (410) is adapted to send a pulse of light, e.g., the stimulating light (e.g., white/visible light) and sense or capture images via a recording light (e.g., infrared light). For example, in some embodiments, the sensor component (410) comprises image sensors (412) and light emitters (414). The image sensors (412) may comprise wafer-level optics (WLO) technology sensors; however, the image sensors (412) are not limited to WLO sensors. In some embodiments, the light emitters (414) comprise light emitting diodes (LEDs); however, the light emitters (414) are not limited to LEDs. The light emitters (414) and image sensors (412) may be arranged in any appropriate configuration. The sensor component (410) may provide the stimulating light, which triggers pupil reaction. The sensor component (410) may simultaneously function as a camera or sensor for detecting the recording light (e.g., IR light). The sensor component (410) may be adapted to measure pupil area or diameter, and may detect the velocity and latency (e.g., lag or wait time). For example, the IR light that bounces off the eye may be detected, whereas the IR light that continues through the pupil may not be detected. Based on what is detected, the system may calculate the appropriate pupil reactivity parameters. The system (400) of the present invention may feature components or systems that can filter out or differentiate between recording light that is reflected off the retina from that which is reflected from the iris.

As previously discussed, in some embodiments, the system (400), e.g., the sensor component (410), is operatively connected to a computer processing system and/or a power source via a wire (430) (e.g., for cost-effectiveness). In some embodiments, the system (400), e.g., the sensor component (410), is wirelessly operatively connected to a computer processing system. In some embodiments, the sensor component (410) comprises a battery system. As previously discussed, in some embodiments, the sensor component (410) functions as a camera. In some embodiments, the sensor component (410) is operatively connected to a camera. In some embodiments, the sensor component (410) and/or camera is operatively connected to a computer system that is adapted to measure and records the pupillary constriction (latency, velocity, amplitude) and process the parameters appropriately to provide information usable to surgeons or other medical professionals.

Referring to FIG. 5A, FIG. 5B, and FIG. 5C, in some embodiments, the sensor component (510) comprises image sensors (512) and light emitters (514). The image sensors (512) may comprise wafer-level optics (WLO) technology sensors; however, the image sensors (512) are not limited to WLO sensors. In some embodiments, the light emitters (514) comprise light emitting diodes (LEDs); however, the light emitters (514) are not limited to LEDs. The light emitters (514) and image sensors (512) may be arranged in any appropriate configuration. Note the configuration shown in FIG. 5A, FIG. 5B, and FIG. 5C is not obstructing central vision (vertical dotted line shown in FIG. 5C). As previously discussed, in some embodiments, the system, e.g., the sensor component (510), is operatively connected to a computer processing system and/or a power source via a wire (530) (e.g., for cost-effectiveness). In some embodiments, the system, e.g., the sensor component (510), is wirelessly operatively connected to a computer processing system.

Referring to FIG. 6A, FIG. 6B, and FIG. 6C, in some embodiments, the sensor component (610) comprises image sensors (612), light emitters (614), and a radio-frequency identification (RFID) antenna (616) for wireless connectivity. The image sensors (612) may comprise wafer-level optics (WLO) technology sensors; however, the image sensors (612) are not limited to WLO sensors. In some embodiments, the light emitters (614) comprise light emitting diodes (LEDs); however, the light emitters (614) are not limited to LEDs. The light emitters (614) and image sensors (612) may be arranged in any appropriate configuration. Note the configuration shown in FIG. 6A, FIG. 6B, and FIG. 6C is not obstructing central vision (vertical dotted line in FIG. 6C).

As previously discussed, the system, e.g., the sensor component, etc., may be operatively connected to a computer system, e.g., via a wireless mechanism. In some embodiments, the wireless mechanism comprises a radio-frequency identification (RFID) system, e.g., an RFID antenna (616). In some embodiments, the wireless mechanism is for collecting measurements of the pupillary reactivity. In some embodiments, the wireless mechanism is for providing power to the image sensor or the light emitters. As previously discussed, the image sensors and light emitters may be arranged on the sensor surface such that they do not obstruct a central line of sight, e.g., a line of sight extending through an apex of the sensor component. In some embodiments, the image sensors and light emitters may be arranged on the sensor surface such that they do not obscure central, paracentral, or near peripheral vision. In some embodiments, wireless connectivity and/or sensor and light emitter configurations that do not obstruct vision may be used to allow the system of the present invention to be used in a patient that is awake. For example, the sensor and light emitter configuration may provide minimal obstruction to vision. The wireless connectivity may allow for the patient to be mobile while using the system. The use of wafer-level optic sensors and/or wafer-level packaging sensors may provide for a low-cost and/or very small technology.

The disclosures of the following documents are incorporated in their entirety by reference herein: U.S. Pat. No. 5,297,554; WO 1990/012534; Chateau et al., 1996, Optom Vis Sci 73(12):733-41; Fison et al., 1979, Br J Ophthal 63:195-199; Ellis C J K, 1981, Br J Ophthal 65:754-759; Sautter et al, 1991, Brain Res 565:23-33; Klöcker N et al., 2001, Journal of Neuroscience Methods 110:147-153; Gellrich et al., 2002, Br J Ophthalmol 86:233-237; Bergamin and Kardon, 2003, Invest Ophthalmol Vis Sci 44:1546-1554; Taylor et al., 2003, J Neurosurg 98(1):205-213; Wilhelm and Wilhelm B, 2003, J Neuro-Ophthalmol 23:42-49; Bremner FD, 2004, Eye 18:1175-1181; Lee et al., 2005, Korean Journal of Ophthalmology 19(2):149-152; Swanson et al., 2005, Invest Ophthalmol Vis Sci 46:3737-3741; Thompson H S, 2005, J Neuro-Ophthalmol 25(1):44-49; Fountas et al., 2006, Neurocrit. Care 5:55-60; Franzen et al., 2009, Biol Psychol 80(3):300-305; Kim S J, Kim Y J, Park K H: Eye 23:727-733,2009; Papageorgiou et al, 2009, J Neuro-Ophthalmol 29:33-36; Warga et al., 2009, Vision Research 49:295-300; Yan et al., 2009, Liver Transplantation 15:1718-1727; Ma et al., 2010, Neuroscience Letters 476: 3-8; Chen et al., 2011, Surg Neural Int 2:82; You et al., 2012, PLoS ONE 7(12):e52061; Ortube et al, 2013, Investigative Ophthalmology & Visual Science 54(1):9-18; Zhu et al, 2013, PLoS ONE 8(7):e68935; Chen et al, 2014, SpringerPlus 3:548; Koehler and Wijdicks, 2015, J Neurosurg 122 (2):453-463.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An ocular cranial nerve monitoring system (100) for monitoring pupillary reactivity, said system (100) comprising:
   a. a sensor component (110) comprising a plurality of image sensors (112) and a plurality of light emitters (114) disposed directly on a sensor component surface, the light emitters (114) are adapted to emit both a stimulating light having a wavelength that is effective for triggering pupil reactivity, and a recording light effective to be reflected from an iris and detected by the image sensors (112), wherein the sensor component senses and captures images via the recording light;
   b. an intermediate plate (120) having a sensor surface and a curved eye surface for placing atop the eye, wherein the sensor surface is attached to the sensor component (110) such that the sensor component surface of the sensor component is disposed directly on and surface-to-surface contacting the sensor surface of the intermediate plate, wherein the intermediate plate allows or promotes transmission of recording light reflected from the iris to the image sensors (112); and
   c. a computer system operatively connected to the image sensors (112), the computer system is adapted to calculate a pupillary reactivity parameter based on recording light detected by the image sensors;
   wherein the system continuously activates the sensor component (110) so as to obtain continuous measurements of the pupillary reactivity parameter.

2. The system (100) of claim 1, wherein the image sensors (112) and light emitters (114) are arranged on the sensor surface in an alternating pattern.

3. The system (100) of claim 1, wherein the image sensors (112) and light emitters (114) are arranged on the sensor surface such that they do not obstruct a line of sight extending through an apex of the sensor component.

4. The system (200) of claim 1, wherein the image sensors (212) and light emitters (214) are arranged on the sensor surface at locations that do not obstruct central vision, paracentral vision, or near peripheral vision.

5. The system (100) of claim 1, wherein the intermediate plate (120) comprises a bundle of optical fibers.

6. The system (100) of claim 1, wherein the intermediate plate (120) comprises a zero-depth optical window.

7. The system (100) of claim 1, wherein the intermediate plate (120) matches curvature of an eye to allow surface tension to hold the system in place when placed on the eye.

8. The system (100) of claim 1 further comprising extensions (320) extending from one or more sides of the sensor component, wherein electrodes (340) are disposed on ends of the extensions (320), the electrodes (340) function to stimulate muscles around the eye.

9. The system of claim 1, wherein the computer system is operatively connected to the sensors via a wireless mechanism.

10. An ocular cranial nerve monitoring system (200) for monitoring pupillary reactivity, said system (200) comprising:
   a. a sensor component (210) comprising a concave sensor surface that accommodates the curvature of the eye, and a plurality of image sensors (212) and a plurality of light emitters (214) disposed directly on the concave sensor surface, wherein the light emitters (214) are adapted to emit both a stimulating light having a wavelength that is effective for triggering pupil reactivity, and a recording light effective to be reflected from an iris and detected by the image sensors (112), wherein the sensor component senses and captures images via the recording light; and
   b. a computer system operatively connected to the image sensors (212), the computer system is adapted to calculate a pupillary reactivity parameter based on recording light detected by the image sensors;
   wherein the system continuously activates the sensor component (210) so as to obtain continuous measurements of the pupillary reactivity parameter.

11. The system (200) of claim 10, wherein the concave sensor surface comprises a flexible support material.

12. The system (200) of claim 11, wherein the flexible support material comprises a polymer adapted for flexible electrodes.

13. The system (200) of claim 10, wherein the concave sensor surface matches curvature of an eye to allow surface tension to hold the system in place when placed on the eye.

14. A method of detecting pupillary reactivity, said method comprising: activating on a patient an ocular cranial nerve monitoring system according to claim 10, wherein the light emitters emit stimulating light and recording light to the iris and pupil, the stimulating light triggers pupil reaction, the sensors detect recording light reflected from the iris, and the computer system calculates a pupillary reactivity parameter based on recording light detected by the sensors.

15. A method of monitoring of intracranial pressure, said method comprising: activating on a patient an ocular cranial nerve monitoring system according to claim 10, wherein the light emitters emit stimulating light and recording light to the iris and pupil, the stimulating light triggers pupil reaction, the sensors detect recording light reflected from the iris, and the computer system calculates a pupillary reactivity parameter based on recording light detected by the sensors, wherein the pupillary reactivity parameter is indicative of intracranial pressure.

16. A method of monitoring of integrity or function of cranial nerve (CN) 2, CN 3, or CN 2 and CN3, said method comprising: activating on a patient an ocular cranial nerve monitoring system according to claim 10, wherein the light emitters emit stimulating light and recording light to the iris and pupil, the stimulating light triggers pupil reaction, the sensors detect recording light reflected from the iris, and the computer system calculates a pupillary reactivity parameter based on recording light detected by the sensors, wherein the pupillary reactivity parameter is indicative of CN 2, CN 3, or CN 2 and CN3 integrity or function.

* * * * *